United States Patent
Choi

(10) Patent No.: US 11,149,272 B2
(45) Date of Patent: Oct. 19, 2021

(54) NUCLEIC ACID SIMULTANEOUSLY INHIBITING EXPRESSION OF MTOR GENE AND STAT3 GENE

(71) Applicant: CURIGIN CO., LTD., Seoul (KR)

(72) Inventor: Jin-Woo Choi, Seoul (KR)

(73) Assignee: CURIGIN CO., LTD., Seoul (KR)

( * ) Notice: Subject to any disclaimer, the term of this patent is extended or adjusted under 35 U.S.C. 154(b) by 0 days.

(21) Appl. No.: 16/482,565

(22) PCT Filed: Jan. 29, 2018

(86) PCT No.: PCT/KR2018/001231
§ 371 (c)(1),
(2) Date: Jul. 31, 2019

(87) PCT Pub. No.: WO2018/143626
PCT Pub. Date: Aug. 9, 2018

(65) Prior Publication Data
US 2019/0345497 A1 Nov. 14, 2019

(30) Foreign Application Priority Data

Jan. 31, 2017 (KR) .................. 10-2017-0013661
Jan. 17, 2018 (KR) .................. 10-2018-0005860

(51) Int. Cl.
| | | |
|---|---|---|
| *A61K 48/00* | (2006.01) | |
| *C07H 21/02* | (2006.01) | |
| *C12N 15/113* | (2010.01) | |
| *A61P 35/00* | (2006.01) | |
| *A61K 31/282* | (2006.01) | |
| *A61K 31/7105* | (2006.01) | |
| *A61K 31/713* | (2006.01) | |
| *A61K 33/243* | (2019.01) | |

(52) U.S. Cl.
CPC .......... *C12N 15/113* (2013.01); *A61K 31/282* (2013.01); *A61K 31/713* (2013.01); *A61K 31/7105* (2013.01); *A61K 33/243* (2019.01); *A61P 35/00* (2018.01); *C12N 2310/14* (2013.01); *C12N 2320/30* (2013.01)

(58) Field of Classification Search
CPC ............ C12N 2310/14; C12N 2320/30; C12N 15/113
See application file for complete search history.

(56) References Cited

U.S. PATENT DOCUMENTS 9,487,785 B2 * 11/2016 Rossi .................... G16B 30/00
2017/0260593 A1 * 9/2017 Trumpp ............... A61K 31/517

FOREIGN PATENT DOCUMENTS

| KR | 10-2015-0138554 A | 12/2015 |
| KR | 10-2016-0106507 A | 9/2016 |
| KR | 10-1696704 B1 | 1/2017 |

OTHER PUBLICATIONS

Semenza, Nature Reviews, 3, 2003, 721-732.*
Yi Zhang, et al., "Effects of STAT3 Gene Silencing and Rapamycin on Apoptosis in Hepato-carcinoma Cells", International Journal of Medical Sciences, 2012, pp. 216-224, vol. 9, No. 3.
Xia Pu, et al., "Effects of mTOR-STAT3 on the migra=tion and invasion abilities of hepatoma cell and mTOR-STAT3 expression in liver cancer", Asian Pacific Journal of Tropical Medicine, 2014, pp. 368-372, vol. 7, No. 5.
International Search Report for PCT/KR2018/001231 dated Jun. 4, 2018 [PCT/ISA/210].

* cited by examiner

*Primary Examiner* — Amy H Bowman
(74) *Attorney, Agent, or Firm* — Sughrue Mion, PLLC

(57) ABSTRACT

The present invention relates to a nucleic acid molecule simultaneously inhibiting the expression of mTOR gene and STAT3 gene, and an anticancer pharmaceutical composition comprising the same. More specifically, base-paired siRNA or shRNA of the present invention, designed to simultaneously inhibit the expression of cancer-related mTOR gene and STAT3 gene in order to surmount the problem that siRNA or shRNA does not achieve high therapeutic effects due to the target specificity thereof, has the effect of promoting the death of cancer cells. In addition, the nucleic acid has the effect of synergistically enhancing the apoptosis of cancer cells when used in combination with an anticancer agent, finding useful applications as an anticancer composition or anticancer aid against various carcinomas.

10 Claims, 8 Drawing Sheets

Specification includes a Sequence Listing.

[FIG. 1]
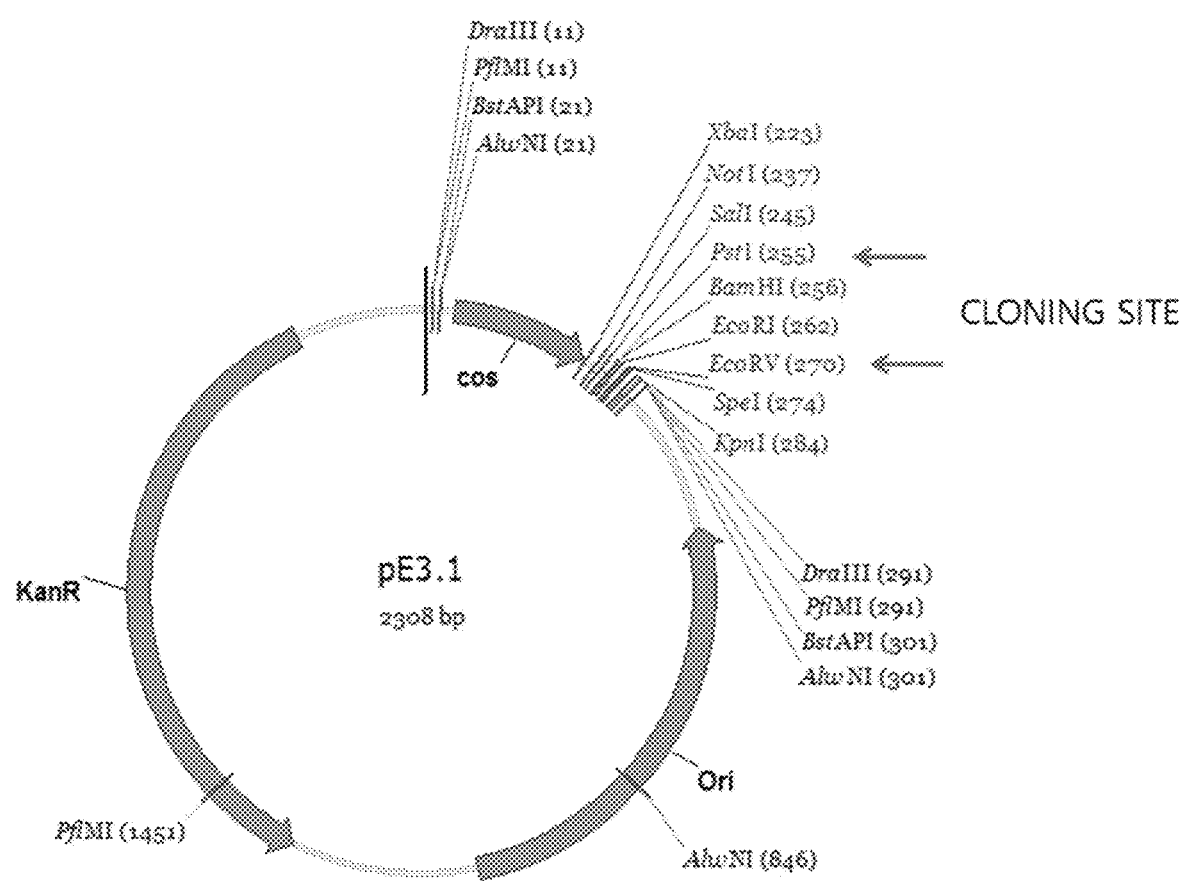

[FIG. 2]
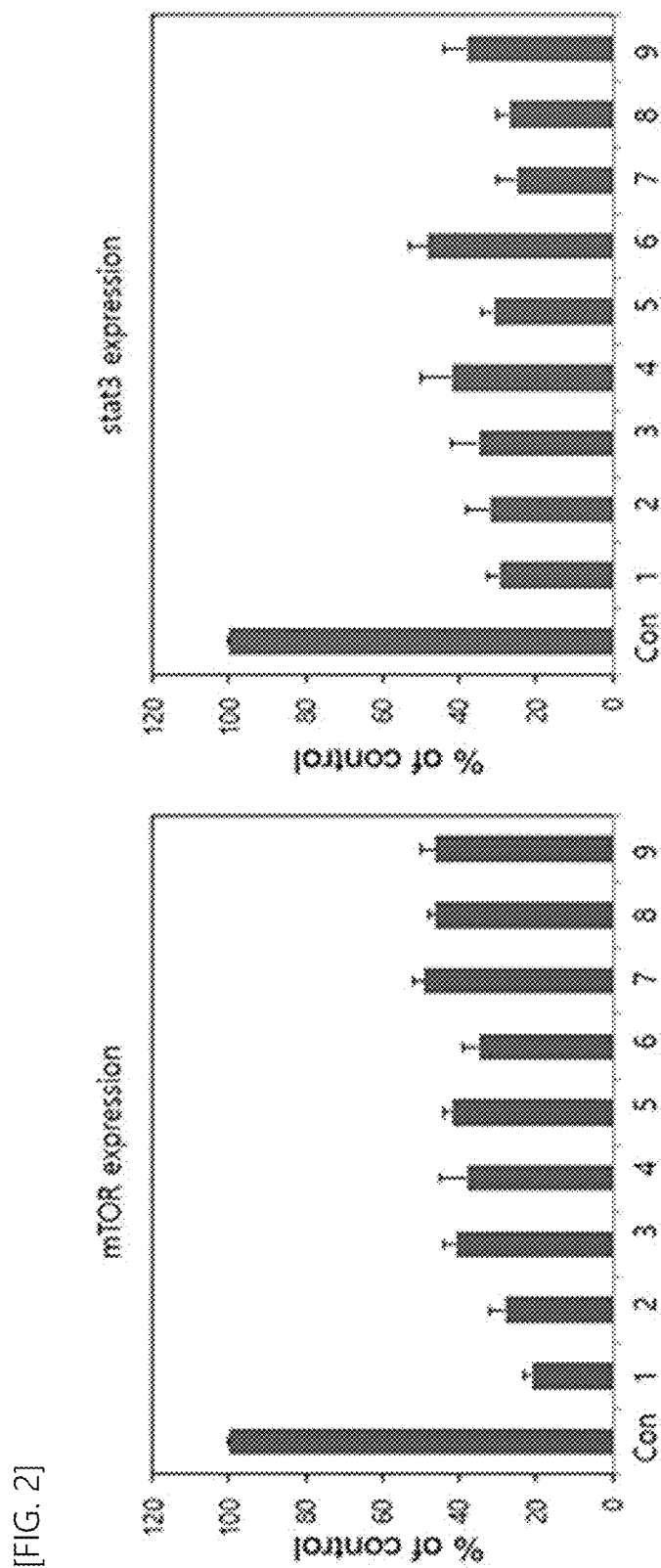

[FIG. 3]
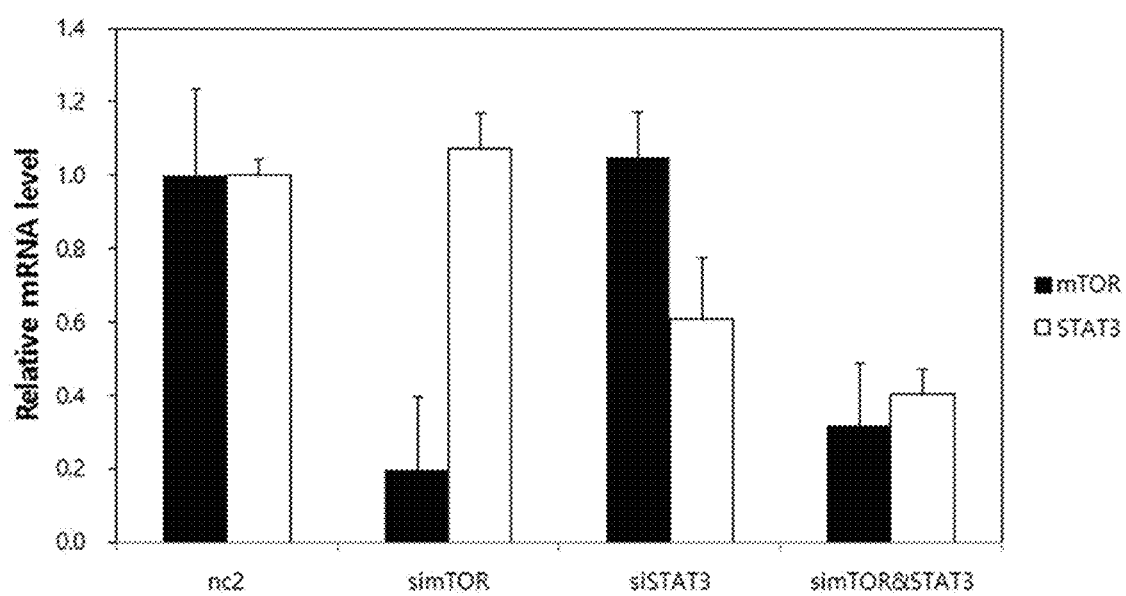

[FIG. 4]
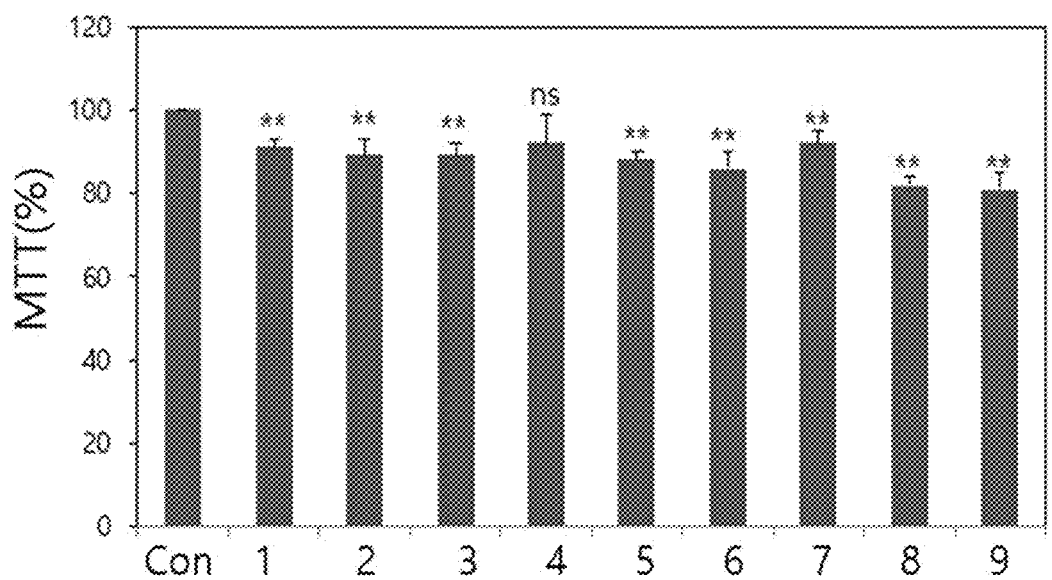

[FIG. 5]
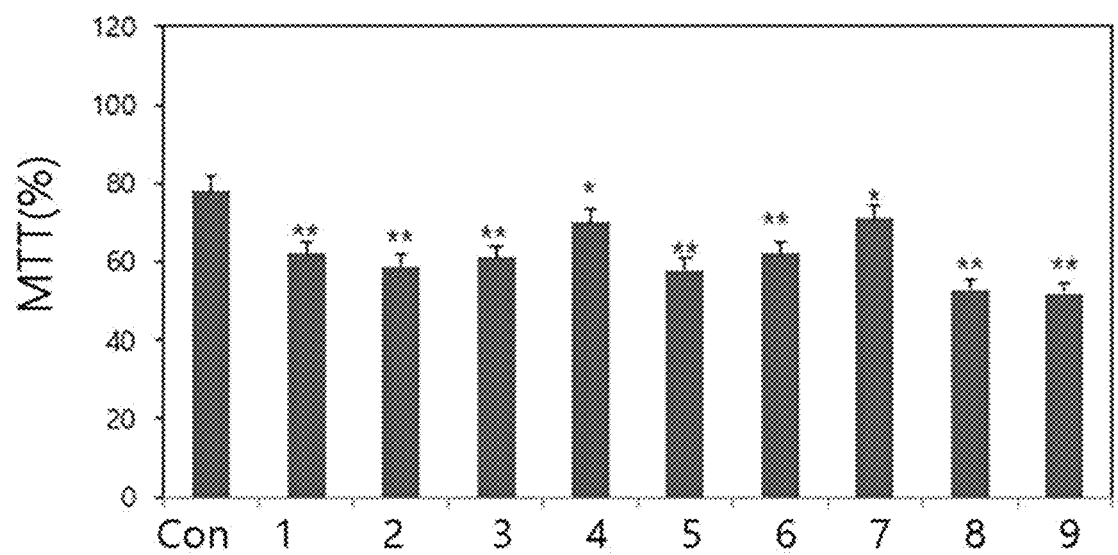

[FIG. 6]
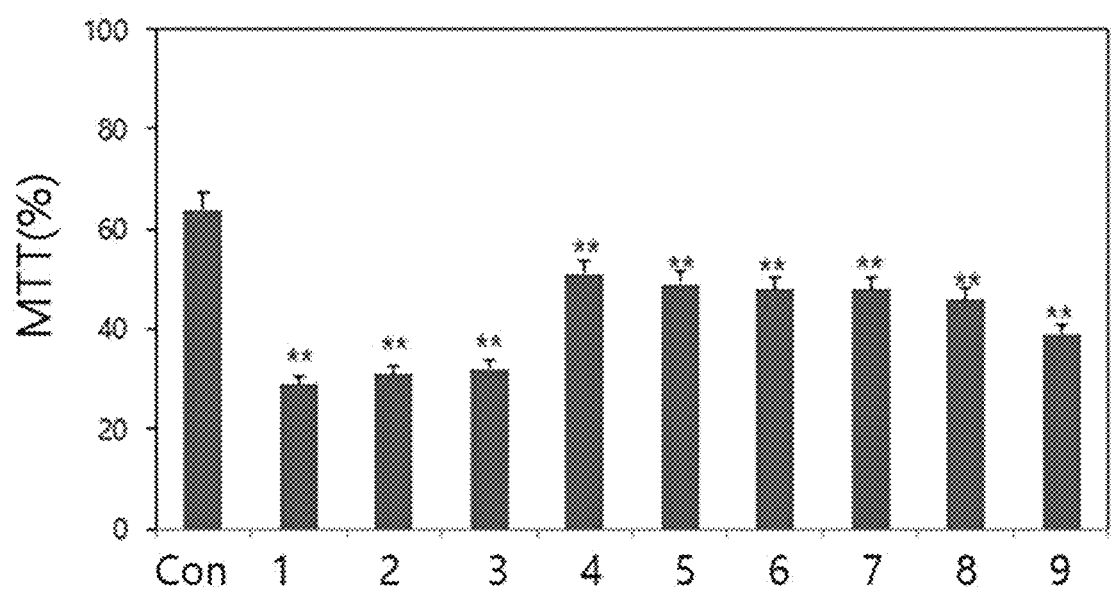

[FIG. 7]
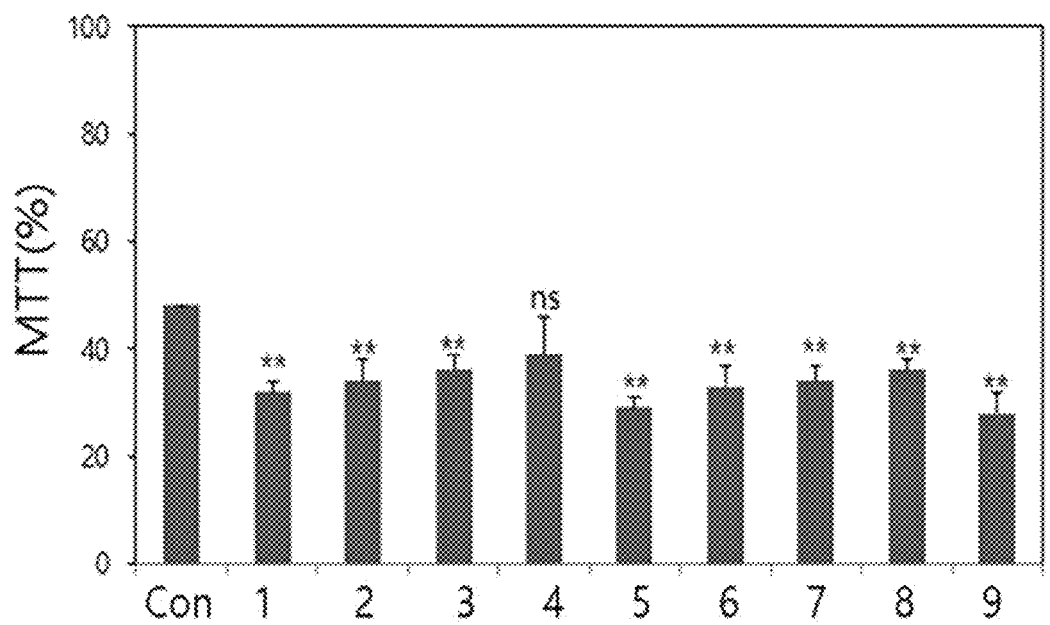

[FIG. 8]
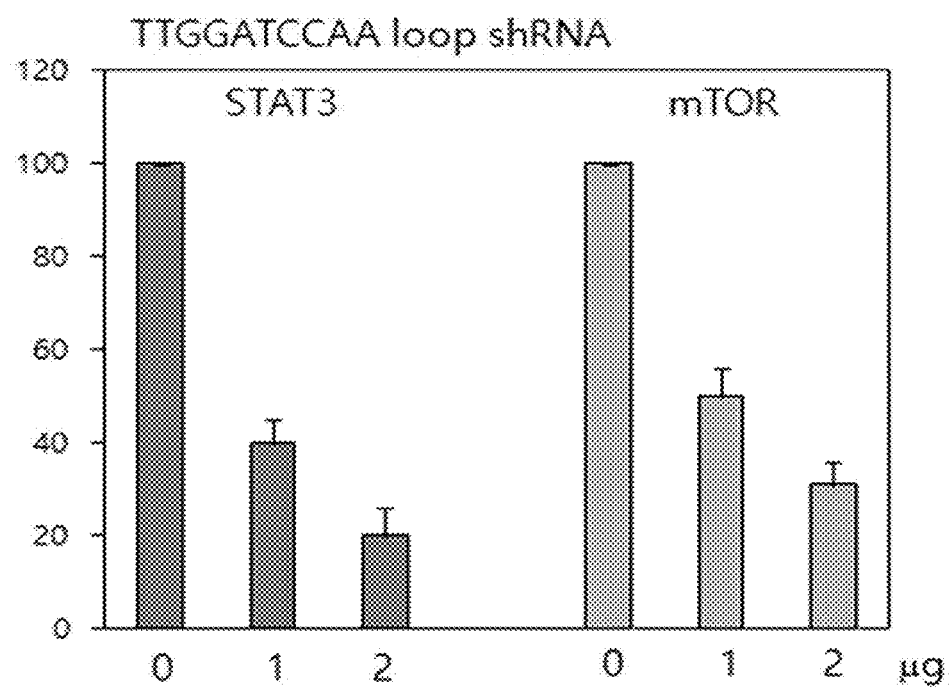
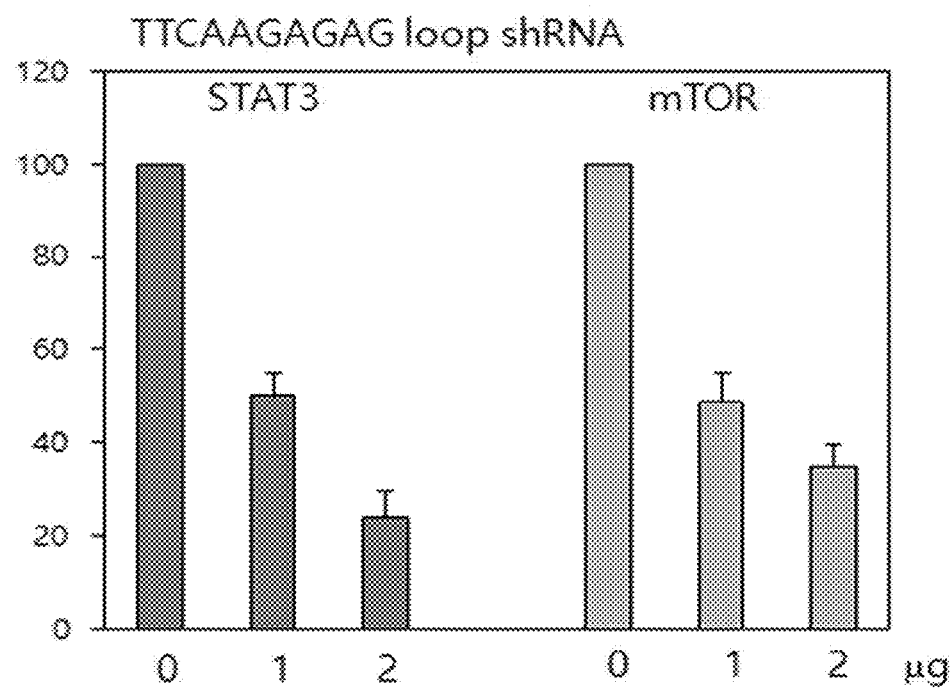

NUCLEIC ACID SIMULTANEOUSLY INHIBITING EXPRESSION OF MTOR GENE AND STAT3 GENE

CROSS REFERENCE TO RELATED APPLICATIONS

This application is a National Stage of International Application No. PCT/KR2018/001231 filed Jan. 29, 2018, claiming priority based on Korean Patent Application No. 10-2017-0013661 filed Jan. 31, 2017 and Korean Patent Application No. 10-2018-0005860 filed Jan. 17, 2018, the entire disclosures of which are incorporated herein by reference.

TECHNICAL FIELD

The present invention relates to a nucleic acid molecule which simultaneously inhibits the expression of mTOR gene and STAT3 gene, and a pharmaceutical composition for anticancer, in which the composition includes the same.

BACKGROUND ART

Cancer is one of diseases that causes the most significant number of deaths all around the world, the development of innovative cancer medicine helps patients to save medical expenses incurred during treatment and allows the medical community to create higher value-added medicines. According to the statistics in 2008, the market size of molecular targeted therapy to overcome drug-resistant problems in existing anticancer drugs was $17.5 billion in seven major countries (US, Japan, France, Germany, Italy, Spain, and UK). It was expected that the size would be about $45 billion, and its growth rate would be 9.5% in 2018 as compared to 2008. Cancer therapy is divided into surgery, radiation therapy, chemotherapy, and biological therapy. For the chemotherapy among them, chemotherapy drugs inhibit the growth of tumor cells or kill them, which has toxicity and harmful effects even on normal cells. Though the anticancer agent causes an immediate reaction, it gradually loses effectiveness after a certain period of time, which is called drug resistance. Thus, it is urgent to develop anticancer drugs that react selectively on tumor cells and has no effect from drug resistance (the present address of combating cancer Biowave 2004. 6 (19)). The new anticancer agents have recently developed, which uses the molecular genetic information and targets molecular properties of cancer. There have been reports that the anticancer drugs for a specific molecular target showed only by cancer cells have no drug resistance.

The technology to inhibit gene expression is an important tool to develop medicines for curing diseases and verify the targets. As the role of RNA interference (hereinafter referred to as RNAi) was revealed, it was found that RNAi reacts with sequence-specific mRNA of diverse kinds of mammalian cells (Silence of the transcripts: RNA interference in medicine. J Mol Med (2005) 83: 764773). RNAi is a phenomenon that inhibits a specific protein expression by specifically combining the small interfering ribonucleic acid (small interfering RNA, hereinafter referred to as siRNA) including a double helical structure having a size of 21 to 25 nucleotides to the mRNA transcript with a complementary sequence and decomposing the corresponding transcripts. In a cell, double-stranded RNA (dsRNA) is processed by an endonuclease being called Dicer to be translated into siRNA with 21 to 23 base pairs (bps). The siRNA combines with RISC (RNA-induced silencing complex), and a guide strand (antisense) recognizes and decomposes targeted mRNA. Thus, these processes specifically interfere the targeted gene expression (NUCLEIC-ACID THERAPEUTICS: BASIC PRINCIPLES AND RECENT APPLICATIONS. Nature Reviews Drug Discovery. 2002. 1, 503-514). According to Bertrand et al., it was found that the siRNA has a more excellent effect of inhibiting expression of the mRNA in vivo and in vitro as compared to the antisense oligonucleotides (ASO) on the same target gene, and the effect is long-lasting. (Comparison of Antisense Oligonucleotides and siRNAs in Cell Culture and in Vivo, Biochem. Biophys. Res. Commun., 296: 1000-1004, 2002). In the global market size, RNAi technology-based therapeutics markets, including siRNA, was analyzed to create more than 12 trillion won by 2020. As the target to apply the technology would be dramatically expanded, it would be evaluated as a future gene therapy technology to treat challenging diseases that are hard to cure with existing antibody- and compound-based medicines. Moreover, as the siRNA mechanism sequence-specifically controls the targeted gene expression by complementary combining with a targeted mRNA, it has a great advantage to develop a lead compound that is optimized to all the targeted protein, including targeted materials which is impossible to make a medicine. While the existing antibody-based medicines or small molecule drugs require longer periods and higher cost to develop and optimize a specifically targeted protein, the siRNA mechanism can be applied to a wider range of targets and reduce the time to develop medicines (Progress Towards in Vivo Use of siRNAs. MOLECULAR THERAPY. 2006 13(4): 664-670). Accordingly, there have been recent studies on selectively inhibiting a specific gene expression in the translation level and developing medicines to cure diverse kinds of disease, specifically the tumor, while RNAi phenomenon provided a possible solution to the problems arising from the existing chemically synthesized medicine development. Furthermore, siRNA-based medicine has another advantage to predict side effect because it has a specific target compared to existing ones. However, in case of tumor caused by various gene problems, the target specificity is a primary cause of impeding the effect of a therapy.

mTOR (mammalian target of rapamycin) is an essential enzyme in a various signal pathway involved in a number of functions, including cytokine-simulating cell growth, translation of mRNA for some principle proteins to regulate the G1 phase of the cell cycle, and transcription of Interleukin-2 (IL-2). Inhibiting mTOR leads to inhibit progression from G1 to S of the cell cycle. As the mTOR inhibitor exhibits immunosuppression, antiproliferative effect, and anticancer activity, mTOR has been used as a target to cure such kinds of diseases (Current Opinion in Lipidology, 16: 317-323, 2005). Also, it plays a crucial role in regulating autophagy, so a number of diseases to regulate self-digestion with mTOR as a target may be treated, for example, cancer, neurodegenerative disorders, heart disease, aging, autoimmune diseases, infectious diseases, Crohn's disease, etc. (Immunology, 7:767-777; Nature 451: 1069-1075, 2008).

STAT3 (signal transducer and activator of transcription 3) is a transcription factor that mediates signals of a variety of growth factors outside of cells and cytokine to the nucleus to activate transcription. STAT3 translocates to the nucleus when it is activated by phosphorylation of a specific tyrosine residue in TAD (transactivation domain) in an inactivated state within the cytoplasm (STAT3 inhibitors for cancer therapy: Have all roads been explored Jak-Stat. 2013; 1; 2(1): e22882). The phosphorylated STAT3 (p-STAT3) make nucleus's DNA binding, which leads wide range of targeted gene expression relating to tumorigenesis such as cell proliferation and differentiation. It is always activated for about 70% of patients with solid cancer and hematologic malignancy (blood cancer) (Role of STAT3 in cancer metastasis and translational advances. BioMed research international. 2013; 2013: 421821). However, as it is hard to find a target inhibiting activation because transcription factor such as STAT3 has three-dimensional structure, it is considered as an undruggable area in conventional new drug synthesis (Transcription Factor STAT3 as a Novel Molecular Target for Cancer Prevention. Cancers. 2014; 16; 6(2): 926-57). Hence, the market demand for siRNA medicines and its delivery system is incredibly high to inhibit STAT3 expression.

Therefore, STAT3 and mTOR have been used as a target for the anticancer agent development since they are major cancer genes that can determine the prognosis in lung cancer, prostate cancer, head and neck cancer, etc. depending on their expression level. However, they exist in the cytoplasm, they cannot be accessed by using the existing antibody therapeutic agents, and systemic side effects are expected to transmit the drug, and thus it is difficult to develop a new drug to suppress them.

DISCLOSURE

Technical Problem

The present invention is directed to providing a nucleic acid that simultaneously inhibits the mTOR gene and the STAT3 gene expression, in order to surmount the problem that siRNA does not achieve high therapeutic effects due to the target specificity thereof, the present invention designs siRNA and shRNA which simultaneously inhibit the mTOR gene and the STAT3 gene expression and confirms their anticancer activity and synergistic anticancer activity with anticancer agent, thereby using them as a pharmaceutical composition for preventing or treating cancer.

Technical Solution

In order to achieve the above object, the present invention provides a nucleic acid molecule that simultaneously inhibits the mTOR and STAT3 genes expression.

Further, the present invention provides a recombinant expression vector including the nucleic acid molecule.

Further, the present invention provides a recombinant microorganism into which the recombinant expression vector is transfected.

Further, the present invention provides a pharmaceutical composition for anticancer, in which the composition includes the nucleic acid molecule as an active ingredient.

Further, the present invention provides a method of preventing and treating cancer, in which the method includes administering to the nucleic acid molecule of claim 1 to a subject in a pharmaceutically effective amount.

Advantageous Effects

According to the present invention, the double-stranded siRNA or shRNA of the present invention includes the sense strand inhibiting the expression of mTOR gene and the antisense strand inhibiting the expression of STAT3 gene to simultaneously inhibit two genes without treating each siRNA or shRNA. Accordingly, they have the effect of promoting the death of cancer cells and synergistically enhancing the apoptosis of cancer cells when used in combination with an anticancer agent, and they are capable of local delivery and are excellent in selectivity so that they can be usefully applied as anticancer compositions or anticancer adjuvants against various carcinomas.

DESCRIPTION OF DRAWINGS

FIG. 1 is a view showing a vector map for expressing shRNAs in a cell, in which the shRNAs include a double-stranded siRNA sequence of the present invention together with a loop sequence in one strand.

FIG. 2 is a view showing the effect of the double-stranded siRNA of the double target of the present invention to inhibit the expression of mTOR or STAT3 gene.

FIG. 3 is a view showing the expression level of mTOR and STAT3 by treating mTOR gene or STAT3 gene with siRNA, respectively or together, in order to verify mutual influence of expression of mTOR gene and STAT3 gene (nc2 is a control siRNA; simTOR is a siRNA targeting the only mTOR; siSTAT3 is a siRNA targeting the only STAT3; and simTOR & STAT3 is co-treated with siRNA targeting mTOR and siRNA targeting STAT3).

FIG. 4 is a view showing the cell survival rate of A549 cells, human lung cancer cell line, when the double target siRNA of the present invention simultaneously inhibits mTOR and STAT3.

FIG. 5 is a view showing the cell survival rate of A549 cells, human lung cancer cell line, when the double target siRNA of the present invention simultaneously inhibits mTOR and STAT3 after treating with cisplatin.

FIG. 6 is a view showing the cell survival rate of A549 cells, human lung cancer cell line, when the double target siRNA of the present invention simultaneously inhibits mTOR and STAT3 after treating with paclitaxel.

FIG. 7 is a view showing the cell survival rate of A549 cells, human lung cancer cell line, when the double target siRNA of the present invention simultaneously inhibits mTOR and STAT3 after treating with 5-fluorouracil (5-FU).

FIG. 8 is a view showing the expression amount of mTOR and STAT3 according to the DNA amount of shRNA by a vector including TTGGATCCAA loop shRNA sequence represented by SEQ ID NO: 20 or TTCAAGAGAG loop shRNA represented by SEQ ID NO: 21.

MODES OF THE INVENTION

The present invention provides a nucleic acid molecule that simultaneously inhibits the expression of mTOR and STAT3 gene.

The nucleic acid molecule may include the nucleotide sequence represented by SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16 or SEQ ID NOs: 17 and 18.

In an embodiment, the nucleotide sequence represented by SEQ ID NOS: 1, 3, 5, 7, 9, 11, 13, 15 and 17 may inhibit the mTOR gene expression by RNA interference, and the nucleotide sequence represented by SEQ ID NOS: 2, 4, 6, 8, 10, 12, 14, 16 and 18 may inhibit the STAT3 gene expression by RNA interference and thus the nucleic acid molecule of the present invention may simultaneously inhibit the expression of mTOR and STAT3 gene.

In an embodiment, it was confirmed that SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS:

11 and 12; SEQ ID NOS: 13 and 14; SEQ ID NOS: 15 and 16; and SEQ ID NOS: 17 and 18, respectively, are designed to be partially complementarily linked to form a double-stranded siRNA, and the double-stranded siRNA targets each of mTOR gene and STAT3 gene to inhibit their expression, thereby verifying that they are double target siRNA set.

In the present invention, the siRNA targeting mTOR or STAT3 has 100% complementary sequence with a part of the mTOR gene or the STAT3 gene of human (*Homo sapiens*) and may degrade mRNA of mTOR gene or STAT3 gene or inhibit its translation.

As used herein, the term "inhibition of expression" means to lead decline in the expression or translation of a target gene, and preferably means that accordingly the expression of the target gene becomes undetectable or resultantly exists at the meaningless level.

As used herein, the term, "small interfering RNA (siRNA)" means short double-stranded RNA capable of inducing RNA interference (RNAi) phenomenon by cleavage of a specific mRNA. Generally, the siRNA consists of a sense RNA strand having a sequence homologous to the mRNA of the target gene and an antisense RNA strand having a complementary sequence thereof. However, in the double-stranded siRNA of the present invention, the sense RNA strand is siRNA (antisense strand to the mTOR gene) consisting of the nucleotide sequences represented by SEQ ID NOS: 1, 3, 5, 7, 9, 11, 13, 15 and 17, and the antisense RNA strand is siRNA (antisense strand to the STAT3 gene) consisting of the nucleotide sequences represented by SEQ ID NOS: 2, 4, 6, 8, 10, 12, 14, 16 and 18 so that the double-stranded siRNA may simultaneously inhibit the expression of the mTOR and the STAT3 gene, respectively. Thus, it can be provided as an efficient method of gene knock-down or gene therapy.

In an embodiment, 17mer of 21mers in siRNA represented by SEQ ID NOS: 1 and 2 of Set 1, 16mer of 20mer in siRNA represented by SEQ ID NOS: 3 and 4 of Set 2, 15mer of 19mer in siRNA represented by SEQ ID NOS: 5 and 6 of Set 3, 14mer of 18mer in siRNA represented by SEQ ID NOS: 7 and 8 of Set 4, and 16mer of 17mer in siRNA represented by SEQ ID NOS: 9 and 10 of Set 5 are complementarily linked. Further, 17mer of 20mer in siRNA represented by SEQ ID NOS: 11 and 12 of Set 6, 16mer of 19mer in siRNA represented by SEQ ID NOS: 13 and 14 of Set 7, 15mer of 18mer in siRNA represented by SEQ ID NOS: 15 and 16 of Set 8, and 15mer of 17mer in siRNA represented by SEQ ID NOS: 17 and 18 of Set 9 are complementarily linked.

Variants of the above nucleotide sequences are included within the scope of the present invention. The nucleic acid molecule of the present invention, which simultaneously inhibits the mTOR and STAT3 gene expression, is used as a concept that includes a functional equivalent of a nucleic acid molecule constituting the nucleic acid molecule, for example, the variant which is capable of performing same function to the nucleic acid molecule although it is modified by the deletion, substitution, or insertion of partial nucleotide sequences of the nucleic acid molecule. Specifically, the gene may include the nucleotide sequence having at least 70%, more preferably at least 80%, even more preferably at least 90%, most preferably at least 95% sequence homology with each nucleotide sequence represented by SEQ ID NOS: 1 to 18. The term "sequence homology percent" to a nucleic acid molecule is determined by comparing the two optimally arranged sequences with the comparison region, and some of the nucleic acid molecule sequences in the comparison region may include addition or deletion (e.g., gap) compared with the reference sequence (without addition or deletion) to the optimal arrangement of the two sequences.

Further, the present invention provides a recombinant expression vector including the nucleic acid molecule.

In order to appropriately transcript the double-stranded siRNA targeting mTOR and STAT3 in target cells in the present invention, it is preferable that the siRNA-containing shRNA, particularly shRNA having a partially modified nucleotide sequence, which is represented by SEQ ID NOS: 1 to 18, is at least operatively linked to the promoter. The promoter may be any one which is capable of functioning in eukaryotic cells. In order to efficiently transcript double-stranded siRNA or shRNA targeting mTOR and STAT3, regulatory sequences may be further included as needed, in which the regulatory sequences include leader sequences, polyadenylation sequences, promoters, enhancers, upstream activation sequences, signal peptide sequences and transcription termination factors. The shRNA may be represented by the nucleotide sequence represented by SEQ ID NO: 20 or 21.

As used herein, the term "short hairpin RNA (shRNA)" means RNA in which single-stranded RNA may partially contain nucleotide sequences having palindrome to form a double-stranded structure in the 3'-region, thereby having a hairpin-like structure, and after expression in cells, it may be cleaved by dicer, which is one type of RNase present in cells to be converted into siRNA. The length of the double-stranded structure is not particularly limited, but is preferably 10 nucleotides or more, and more preferably 20 nucleotides or more. In the present invention, the shRNA may be included in a vector.

As used herein, the term "vector" means a means for expressing a target gene in a host cell, in which it may include plasmid vectors; phagemid vectors; cosmid vectors; and viral vectors such as bacteriophage vectors, adenovirus vectors, retroviral vectors, and adeno-associated viral vectors.

According to a preferred embodiment of the present invention, the gene in the vector of the present invention is operatively linked to a promoter.

As used herein, the term "operably linked" refers to a functional linkage between a gene expression regulatory sequence (e.g., an array of binding site of promoter, signal sequence, or transcription factor) and different gene sequences, and accordingly, the regulatory sequence regulates the transcription and/or translation of the different gene sequences.

The vector system of the present invention may be constructed by various manners known in the art, and these specific manners are disclosed in Sambrook et al. (2001), Molecular Cloning, A Laboratory Manual, Cold Spring Harbor Laboratory Press, and this document is incorporated herein by reference.

The vector of the present invention may typically be constructed as a cloning vector or as an expression vector. Further, the vector of the present invention may be constructed by using a prokaryotic cell or eukaryotic cell as a host. When the vector of the present invention is an expression vector, and a prokaryotic cell is used as a host, it generally includes a strong promoter capable of promoting transcription (e.g., tac promoter, lac promoter, lacUV5 promoter, lpp promoter, pLλ promoter, pRλ promoter, rac5 promoter, amp promoter, recA promoter, SP6 promoter, trp promoter and T7 promoter), a ribosome binding site for initiation of translation and a transcription/translation termination sequence. When *E. coli* (e.g., HB101, BL21, DH5α) is used as a host cell, the promoter and operator site of the E. coli tryptophan biosynthetic pathway (Yanofsky, C. (1984), J. Bacteriol., 158: 1018-1024) and the left promoter of phage λ (pLλ promoter, Herskowitz, I. and Hagen, D. (1980), Ann. Rev. Genet., 14: 399-445) may be used as a regulatory site.

Meanwhile, the vector that may be used for the present invention can be manufactured by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like), a phagemid (for example, pComb3X), a phage or a virus (for example, SV40 or the like) often used in the art.

Meanwhile, when the vector of the present invention is an expression vector, and a eukaryotic cell is used as a host, a promoter derived from a genome of a mammalian cell (for example, a metallothionein promoter) or a promoter derived from a mammalian virus (for example, adenovirus late promoter, vaccinia virus 7.5K promoter, SV40 promoter, cytomegalovirus promoter and HSV tk promoter) can be used, and it generally contains a polyadenylation sequence as a transcription termination sequence.

In order to readily purify protein, the vector of the present invention may be fused with other sequences as needed. The fusion sequence includes, for example, glutathione S-transferase (Pharmacia, USA), maltose binding protein (NEB, USA), FLAG (IBI, USA), and 6× His (hexahistidine; Quiagen, USA), but is not limited thereto. Further, the expression vector of the present invention may include an antibiotic resistance gene commonly used in the art as a selection marker, and the resistance gene includes, for example, resistance genes against ampicillin, gentamycin, carbenicillin, chloramphenicol, streptomycin, kanamycin, geneticin, neomycin and tetracycline.

Further, the present invention provides a recombinant microorganism into which the recombinant expression vector is transfected.

Any kind of a host cell known in the pertinent art can be used if stable and continuous cloning and expression of the vector of the present invention can be achieved by using it. Examples include a prokaryotic host cell including strains belonging to the genus Bacillus such as Escherichia coli, Bacillus subtilus and Bacillus thuringiensis, Streptomyces, Pseudomonas (for example, Pseudomonas putida), Proteus mirabilis or Staphylococcus (for example, Staphylococcus carnosus), but is not limited thereto. The host cell is preferably E. coli, and more preferably E. coli ER2537, E. coli ER2738, E. coli XL-1 Blue, E. coli BL21(DE3), E. coli JM109, E. coli DH series, E. coli TOP10, E. coli TG1 and E. coli HB101.

Methods of transfecting the vector of the present invention into a host cell may be carried out by the CaCl2 method (Cohen, S N et al. (1973), Proc. Natl. Acac. Sci. USA, 9: 2110-2114), Hanahan's method (Cohen, S. N. et al. (1973), Proc. Natl. Acac. Sci. USA, 9:2110-2114; and Hanahan, D. (1983), J. Mol. Biol., 166:557-580), an electroporation method (Dower, W. J. et al. (1988), Nucleic Acids Res., 16: 6127-6145) and the like.

Further, the present invention provides a pharmaceutical composition for anticancer, in which the composition includes the nucleic acid molecule as an active ingredient.

The nucleic acid molecule may further include an anticancer agent, for example, acivicin, aclarubicin, acodazole, achromycin, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus Calmette-Guerin (BCG), Baker's antifol, β-2-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, Corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, dedatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5'-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, 4-ipomeanol, iproplatin, isotretinoin, leucovorin calcium, leuprolide acetate, levamisole, liposome daunorubicin, liposome-encapsulated doxorubicin, lomustine, lonidamine, maytansine, mechlorethamine hydrochloride, melphalan, menogaril, merbarone, 6-mercaptopurine, mesna, methanol extraction of Bacillus Calmette-Guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, cytosine arabinoside, etoposide, melphalan, taxol and mixtures thereof. It includes preferably cisplatin, paclitaxel, 5-fluorouracil (5-FU), methotrexate, doxorubicin, daunorubicin, cytosine arabinoside, etoposide, melphalan, chlorambucil, cyclophosphamide, vindesine, mitomycin, bleomycin, tamoxifen, and taxol, and more preferably cisplatin, paclitaxel, 5-fluorouracil (5-FU), but is not limited thereto in order to achieve the object of showing a synergistic effect on the anticancer effect by co-treating with the nucleic acid molecule of the present invention.

The cancer may be any one selected from the group consisting of colon cancer, breast cancer, uterine cancer, cervical cancer, ovarian cancer, prostate cancer, brain tumor, head and neck carcinoma, melanoma, myeloma, leukemia, lymphoma, gastric cancer, lung cancer, pancreatic cancer, non-small cell lung cancer, liver cancer, esophageal cancer, small intestine cancer, anal cancer, fallopian tube cancer, endometrial cancer, vaginal cancer, vulva cancer, Hodgkin lymphoma, bladder cancer, kidney cancer, ureter cancer, kidney cell carcinoma, kidney pelvic carcinoma, bone cancer, skin cancer, head cancer, cervical cancer, skin melanoma, choroidal melanoma, endocrine gland cancer, thyroid carcinoma, parathyroid gland cancer, adrenal cancer, soft tissue sarcoma, urethral cancer, penile cancer, central nervous system (CNS) tumor, primary CNS lymphoma, spinal cord tumor, polymorphic glioblastoma and pituitary adenoma.

The pharmaceutical composition of the present invention may further include an adjuvant in addition to the single domain antibody. The adjuvant can be used without limitation as long as it is known in the art. However, it can include, for example, Freund's complete or incomplete adjuvants to enhance its effectiveness The pharmaceutical composition according to the present invention may be produced in the form of incorporation of an active ingredient into a pharmaceutically acceptable carrier. In this regard, the pharmaceutically acceptable carrier includes a carrier, excipient and diluent commonly used in the pharmaceutical field. Pharmaceutically acceptable carriers for use in the pharmaceutical compositions of the present invention include, but are not limited to, lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methyl hydroxybenzoate, propyl hydroxybenzoate, talc, magnesium stearate and mineral oil.

The pharmaceutical composition of the present invention may be formulated in the form of oral preparations such as powder, granule, tablet, capsule, suspension, emulsion, syrup or aerosol, external preparation, suppositories or sterilized injection solutions according to each conventional method.

Formulations can be prepared by using generally used excipients or diluents such as fillers, extenders, binders, wetting agents, disintegrating agents and surfactant. Solid formulations for oral administration include tablets, pills, powders, granules and capsules. These solid formulations are prepared by mixing one or more excipients such as starch, calcium carbonate, sucrose, lactose and gelatin to active ingredients. Except for the simple excipients, lubricants, for example magnesium stearate, and talc can be used. Liquid formulations for oral administrations include suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration include sterilized aqueous solutions, water-insoluble excipients, suspensions, emulsions, lyophilized preparations and suppositories. Water-insoluble excipients and suspensions can include propylene glycol, polyethylene glycol, vegetable oil like olive oil, injectable ester like ethylolate, etc. Suppositories can include witepsol, tween 61, cacao butter, laurin butter, glycerogelatin, etc.

The pharmaceutical composition according to the present invention may be administered to a subject by various routes. All modes of administration may be expected, for example, by oral, intravenous, intramuscular, subcutaneous, intraperitoneal injection.

The administration amount of the pharmaceutical composition according to the present invention is selected in consideration of the age, weight, sex, physical condition, etc. of the subject. It is apparent that the concentration of the single domain antibody included in the pharmaceutical composition may be variously selected depending on the subject. It is preferably included in the pharmaceutical composition at a concentration of 0.01 µg/ml to 5,000 µg/ml. When the concentration is less than 0.01 µg/ml, the pharmaceutical activity may not be exhibited. When the concentration is more than 5,000 µg/ml, it may be toxic to the human body.

The pharmaceutical composition of the present invention may be used for preventing or treating cancer and complications thereof and can also be used as an anticancer adjuvant.

Further, the present invention provides a method of preventing and treating cancer, in which the method includes administering to a subject the nucleic acid molecule of claim 1 in a pharmaceutically effective amount.

The pharmaceutical composition of the present invention is administered in therapeutically or pharmaceutically effective amounts. The term "pharmaceutically effective amount" means an amount sufficient to treat a disease at a reasonable benefit/risk ratio applicable to medical treatment. The effective dose level may be determined by factors such as the subject's species, severity, age, sex, drug activity, drug sensitivity, the time of administration, the route of administration, the rate of excretion, the duration of the treatment and co-administered drugs, and other factors well known in the medical arts.

The present invention is described in more detail with reference to the following Examples. However, the following Examples are only for the purpose of illustrating the present invention, and therefore, the present invention is not limited thereto.

EXAMPLE 1

Preparation of Double Target siRNA

The double target siRNA (double strand) which is capable of simultaneously inhibiting signal transducer and activator of transcription 3 (STAT3) and mammalian target of rapamycin (mTOR) was prepared by sequences as shown in Table 1 below (Bioneer, Daejeon, Korea).

TABLE 1

| set | siRNA | Sequence | Length | SEQ ID NO. |
|---|---|---|---|---|
| 1 | antisense_mTOR(5'→3') | gacuguggcauccaccugcau | 21 | 1 |
|   | antisense_STAT3 (3'→5') | cugacuccgcggauggacgua |  | 2 |
| 2 | antisense_mTOR(5'→3') | gacuguggcauccaccugca | 20 | 3 |
|   | antisense_STAT3 (3'→5') | cugacuccgcggauggacgu |  | 4 |
| 3 | antisense_mTOR(5'→3') | gacuguggcauccaccugc | 19 | 5 |
|   | antisense_STAT3 (3'→5') | cugacuccgcggauggacg |  | 6 |

TABLE 1-continued

| set | siRNA | Sequence | Length | SEQ ID NO. |
|---|---|---|---|---|
| 4 | antisense_mTOR(5'→3') | gacuguggcauccaccug | 18 | 7 |
|   | antisense_STAT3 (3'→5') | cugacuccgcggauggac |   | 8 |
| 5 | antisense_mTOR(5'→3') | caagcugcuguggcuga | 17 | 9 |
|   | antisense_STAT3 (3'→5') | guucgacgacaucgacu |   | 10 |
| 6 | antisense_mTOR(5'→3') | ugcugggccgcaugcgcugc | 20 | 11 |
|   | antisense_STAT3 (3'→5') | acgacccggcgucaccgacg |   | 12 |
| 7 | antisense_mTOR(5'→3') | gcugggccgcaugcgcugc | 19 | 13 |
|   | antisense_STAT3 (3'→5') | cgacccggcgucaccgacg |   | 14 |
| 8 | antisense_mTOR(5'→3') | cugggccgcaugcgcugc | 18 | 15 |
|   | antisense_STAT3 (3'→5') | gacccggcgucaccgacg |   | 16 |
| 9 | antisense_mTOR(5'→3') | ugggccgcaugcgcugc | 17 | 17 |
|   | antisense_STAT3 (3'→5') | acccggcgucaccgacg |   | 18 |

17mer of 21mers in siRNA represented by SEQ ID NOS: 1 and 2 of Set 1, 16mer of 20mer in siRNA represented by SEQ ID NOS: 3 and 4 of Set 2, 15mer of 19mer in siRNA represented by SEQ ID NOS: 5 and 6 of Set 3, 14mer of 18mer in siRNA represented by SEQ ID NOS: 7 and 8 of Set 4, and 16mer of 17mer in siRNA represented by SEQ ID NOS: 9 and 10 of Set 5 are complementarily linked. Further, 17mer of 20mer in siRNA represented by SEQ ID NOS: 11 and 12 of Set 6, 16mer of 19mer in siRNA represented by SEQ ID NOS: 13 and 14 of Set 7, 15mer of 18mer in siRNA represented by SEQ ID NOS: 15 and 16 of Set 8, and 14mer of 17mer in siRNA represented by SEQ ID NOS: 17 and 18 of Set 9 are complementarily linked.

Specifically, after two sequences of each set are introduced into cells in the form of a double strand, the siRNA of antisense_mTOR of each set is complementarily linked to the target site of mTOR mRNA (gi|206725550|ref|NM_004958.3| *Homo sapiens* mechanistic target of rapamycin (serine/threonine kinase) (MTOR), mRNA).

Further, siRNA of antisense_STAT3 of each set is complementarily linked to the target site of STAT mRNA (gi|47080104|ref|NM_139276.2| *Homo sapiens* signal transducer and activator of transcription 3 (acute-phase response factor) (STAT3), transcript variant 1, mRNA), thereby inhibiting mTOR and STAT3 gene expression.

EXAMPLE 2

Preparation of shRNA Including Double Target siRNA

In order to be able to express the double target siRNA represented by SEQ ID NOS: 1 and 2 of Set 1 prepared in Example 1 in cells, shRNAs containing the siRNA double strand sequence and the loop sequence (TTGGATCCAA loop shRNA and TTCAAGAGAG loop shRNA) (Table 2) were constructed. Each of the constructed shRNAs was placed following the U7 promoter (SEQ ID NO: 19) at the cleavage sites of the restriction enzymes Pst I and Eco RV of the pE3.1 vector (FIG. 1), thereby constructing recombinant expression vectors which are capable of expressing two shRNAs including double target siRNA targeting mTOR and STAT3 in the cells.

TABLE 2

| shRNA | nucleic acid molecule sequence(5'→3') | SEQ ID NO. |
|---|---|---|
| UUGGAUCCAA shRNA | loopgactgtggcatccacctgcatTTGGATCCAA atgcaggtaggcgcctcagtcTT | 20 |
| UUCAAGAGAG shRNA | loopgactgtggcatccacctgcatTTCAAGAGAG atgcaggtaggcgcctcagtcTT | 21 |

EXPERIMENTAL EXAMPLE 1

Confirmation of mTOR and STAT3 Gene Expression Inhibitory Effect By Double Target siRNA Hela cells were seeded on a 12-well plate. Then, until the cell confluent reached 50%, the cells were cultured in RPMI medium (Hyclone) supplemented with 10% FBS (Hyclone) at 37° C. and 5% CO$_2$. Then, the cells were transfected with the double target siRNA prepared in Example 1 using lipofectamine 3000 (Invitrogen, Carlsbad, Calif., USA) to perform the know-down of Bcl1, Bl1, AR, mTOR and STAT3, simultaneously. After 48 hours of the transfection, the cells were disrupted, and total RNAs were extracted with GeneJET RNA Purification Kit (Invitrogen). The reverse transcription was performed with RevoScript™ RT PreMix (iNtRON BIOTECHNOLOGY) using the extracted total RNA as a template.

20 μl of a sample containing 25 to 200 ng of the reverse transcribed cDNA, AmpONE taq DNA polymerase (Gene-All) and TaqMan Gene Expression assays (Applied Biosystems) were used. They were reacted with MTOR (Hs00234522_m1), STAT3 (Hs01047580_m1) and GAPDH (Hs02758991_g1) using ABI PRISM 7700 Sequence Detection System and QS3 Real-time PCR (Biosystems). The real-time PCR reaction conditions were [2 minutes at 50° C., 10 minutes at 95° C., and two cycles of 15 seconds at 95° C. and 60 seconds at 60° C.], and the reaction was repeated in total 40 cycles. All reactions were repeated three times, and the mean value of these was obtained. The results were normalized to the mRNA values of the housekeeping gene GAPDH.

As a result, it was confirmed that mTOR and STAT3 had 20% to 40% residual expression compared to the control by double target siRNAs of Sets 1 to 9, and it was found that the double target siRNA simultaneously inhibited expression of both genes (FIG. 2).

EXAMPLE 2

Preparation of Recombinant Expression Vectors Expressing shRNA Including Double Target siRNA In order to express the double target siRNA represented by SEQ ID NOS: 1 and 2 of Set 1 prepared in Example 1 in cells, nucleic acid molecules encoding shRNAs containing the siRNA double strand sequence and the loop sequence UUGGAUCCAA loop shRNA and UUCAAGAGAG loop shRNA) were constructed (each nucleic acid molecule sequence is respectively shown in SEQ ID NOS: 20 and 21 of Table 2). Each nucleic acid molecule was placed following the U7 promoter (SEQ ID NO: 19) at the cleavage sites of the restriction enzymes Pst I and Eco RV of the pE3.1 vector (FIG. 1), thereby constructing recombinant expression vectors which are capable of expressing two shRNAs including double target siRNA targeting mTOR and STAT3 in the cells (each shRNA sequence is respectively shown in SEQ ID NOS: 26 and 27).

TABLE 3

| | | sequence (5'→3') | SEQ No. |
|---|---|---|---|
| mTOR siRNA | sense strand | GUGGAAACAGGACCCAUGA(dTdT) | 22 |
| | antisense strand | UCAUGGGUCCUGUUUCCAC(dTdT) | 23 |
| STAT3 siRNA | sense strand | UGUUCUCUGAGACCCAUGA(dTdT) | 24 |
| | antisense strand | UCAUGGGUCUCAGAGAACA(dTdT) | 25 |

TABLE 4

| | mTOR | std dev | STAT3 | std dev |
|---|---|---|---|---|
| nc2 | 1.0000 | 0.318658 | 1.0000 | 0.287738516 |
| simTOR | 0.1980 | 0.076805 | 1.0705 | 0.251995803 |
| siSTAT3 | 1.0507 | 0.40253 | 0.6074 | 0.120361215 |
| simTOR&STAT3 | 0.3174 | 0.046248 | 0.4022 | 6.7987E−17 |

As a result, the mTOR and STAT3 expression were decreased by each siRNA. The result was compared with the case of co-treating with both siRNAs, indicating that the mTOR gene and STAT3 expression did not mutually affect (FIG. 3 and Table 4).

EXPERIMENTAL EXAMPLE 3

Confirmation of Cancer Cell Death By Double Target siRNA

In order to confirm effects on cancer cell death by double target siRNA of Sets 1 to 9 of the present invention, human lung cancer cell line A549 cells were seeded to $5 \times 10^3$ cells/well in a 96-well plate, and then the cells were transfected with the double target siRNA (mTOR and STAT3 co-knock down) using lipofectamine 3000. After 48 hours of the transfection and additional 24 hours, the cells were treated with 5 mg/mL MTT (Promega, Ltd.) and incubated for 4 hours. Thereafter, the medium was removed, and the cells were treated with 150 µl of solubilization solution and stop solution and incubated at 37° C. for 4 hours. The absorbance of the reaction solution was measured at 570 nm, and the cell viability was calculated using the following equation.

$$\text{Cell viability} = \text{absorbance of experimental group (570 nm)/absorbance of control group (570 nm)} \times 100(\%) \quad \text{[Equation]}$$

As a result, it was confirmed that when mTOR and STAT3 were simultaneously inhibited by the double target siRNA of the present invention, the cell viability was significantly reduced as compared to the control group. Therefore, it was confirmed that the double target siRNA of Sets 1 to 9 of the present invention effectively led to the cancer cell death (FIG. 4).

EXPERIMENTAL EXAMPLE 4

Confirmation of Cancer Cell Death By Co-Treatment with Double Target siRNA and Anticancer Agent 4-1. Co-Treatment with Cisplatin Human lung cancer cell line A549 cells were seeded at $5 \times 10^3$ cells/well in 96-well plates. Then, the cells were transfected with each of the double target siRNAs (mTOR and STAT3 co-knock down) using lipofectamine 3000. After 48 hours of the transfection, the cells were treated with 5 µM of cisplatin and incubated for 10 hours. Thereafter, the MTT reaction was performed as in Experimental Example 3, and the absorbance thereof was measured at 570 nm to calculate the cell viability.

As a result, it was confirmed that when mTOR and STAT3 were simultaneously inhibited by the double-target siRNA of Sets 1 to 9 of the present invention in combination with cisplatin, the cell viability was reduced to about 50% to 70%, and there was a significant difference compared to the control group. Therefore, it was confirmed that when the two genes were simultaneously inhibited even in combination with the anticancer agent, the cell death effect was significantly improved (FIG. 5).

4-2. Co-Treatment with Paclitaxel

Human lung cancer cell line A549 cells were seeded at $5 \times 10^3$ cells/well in 96-well plates. Then, the cells were transfected with each of the double target siRNAs (mTOR and STAT3 co-knock down) using lipofectamine 3000. After 48 hours of the transfection, the cells were treated with 5 µM of paclitaxel and incubated for 10 hours. Thereafter, the MTT reaction was performed as in Experimental Example 3, and the absorbance thereof was measured at 570 nm to calculate the cell viability.

As a result, it was confirmed that when mTOR and STAT3 were simultaneously inhibited by the double-target siRNA of Sets 1 to 9 of the present invention in combination with paclitaxel, the cell viability was reduced to about 30% to 50%, and there was a significant difference compared to the control group. Therefore, it was confirmed that when the two genes were simultaneously inhibited even in combination with the anticancer agent, the cell death effect was significantly improved (FIG. 6).

4-3. Co-Treatment with 5-fluorouracil (5-FU)

Human lung cancer cell line A549 cells were seeded at $5\times10^3$ cells/well in 96-well plates. Then, the cells were transfected with each of the double target siRNAs (mTOR and STAT3 co-knock down) using lipofectamine 3000. After 48 hours of the transfection, the cells were treated with 1 μM of 5-fluorouracil and incubated for 10 hours. Thereafter, the MTT reaction was performed as in Experimental Example 3, and the absorbance thereof was measured at 570 nm to calculate the cell viability.

As a result, it was confirmed that when mTOR and STAT3 were simultaneously inhibited by the double-target siRNA of Sets 1 to 9 of the present invention in combination with 5-fluorouracil, the cell viability was reduced to about 30%, and there was a significant difference compared to the control group. Therefore, it was confirmed that when the two genes were simultaneously inhibited even in combination with the anticancer agent, the cell death effect was significantly improved (FIG. 7).

EXPERIMENTAL EXAMPLE 5 mTOR and STAT3 Inhibitory Effect of shRNA Including Double Target siRNA

A549 cells were transfected with 0, 1 and 2 μg of the vector containing the TTGGATCCAA loop shRNA sequence represented by SEQ ID NO: 20 or the TTCAAGAGAG loop shRNA represented by SEQ ID NO: 21 prepared in Example 2 using lipofectamine 3000. After 48 hours of the transfection, the decrease level in mTOR and STAT3 gene expression was confirmed using the real time PCR analysis method as described in Experimental Example 1.

As a result, the expression of mTOR and STAT3 was decreased in both shRNAs containing the double target siRNA of the present invention, and the level showed a downward tendency to about 20% in proportion to the DNA amount of shRNA (FIG. 8).

---

The invention claimed is:

1. A method of treating cancer, the method comprising administering a nucleic acid molecule which simultaneously inhibits an expression of mammalian target of rapamycin (mTOR) gene and an expression of signal transducer and activator of transcription 3 (STAT3) gene to a subject in need thereof in a pharmaceutically effective amount,
wherein the nucleic acid molecule includes nucleotide sequences represented by SEQ ID NOs: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16; or SEQ ID NOs: 17 and 18,
wherein the cancer is selected from the grouping consisting of lung cancer, glioblastoma multiforme (GBM) and bladder cancer.

2. The method according to claim 1, wherein the nucleotide sequences represented by SEQ ID NOS: 1, 3, 5, 7, 9, 11, 13, 15 and 17 inhibit the expression of the mTOR gene by RNA interference.

3. The method according to claim 1, wherein the nucleotide sequences represented by SEQ ID NOS: 2, 4, 6, 8, 10, 12, 14, 16 and 18 inhibit the expression of the STAT3 gene by RNA interference.

4. The method according to claim 1, wherein SEQ ID NOS: 1 and 2; SEQ ID NOS: 3 and 4; SEQ ID NOS: 5 and 6; SEQ ID NOS: 7 and 8; SEQ ID NOS: 9 and 10; SEQ ID NOS: 11 and 12; SEQ ID NOS: 13 and 14; SEQ ID NOS: 15 and 16; and SEQ ID NOS: 17 and 18, respectively, are partially complementarily linked to form a double-stranded siRNA.

5. The method according to claim 1, wherein the nucleic acid molecule is a short hairpin RNA (shRNA).

6. The method according to claim 5, wherein the shRNA is represented by the nucleotide sequence represented by SEQ ID NO: 20 or SEQ ID NO: 21.

7. The method according to claim 5, wherein the nucleic acid molecule is administered in a form of a recombinant expression vector which includes a DNA molecule where the sequence of the shRNA is modified by replacing uracil with thymine.

8. The method according to claim 1, wherein the nucleic acid molecule is administered in a form of a pharmaceutical composition for anticancer which includes the nucleic acid molecule as an active ingredient.

9. The method according to claim 8, wherein the pharmaceutical composition further includes an anticancer agent.

10. The method according to claim 9, wherein the anticancer agent is at least one selected from the group consisting of cisplatin, paclitaxel, 5-fluorouracil (5-FU), methotrexate, doxorubicin, daunorubicin, cytosine arabinoside, etoposide, melphalan, chlorambucil, cyclophosphamide, vindesine, mitomycin, bleomycin, tamoxifen, and taxol.

* * * * *

SEQUENCE LISTING

<160> NUMBER OF SEQ ID NOS: 27

<210> SEQ ID NO 1
<211> LENGTH: 21
<212> TYPE: RNA
<213> ORGANISM: Artificial Sequence
<220> FEATURE:
<223> OTHER INFORMATION: antisense_mTOR of set 1

<400> SEQUENCE: 1
gacuguggca uccaccugca u                                                  21

<210> SEQ ID NO 2
<211> LENGTH: 21
<212> TYPE: RNA
<213> ORGANISM: Artificial Sequence
<220> FEATURE:
<223> OTHER INFORMATION: antisense_STAT3 of set 1

<400> SEQUENCE: 2
augcagguag gcgccucagu c                                                  21

<210> SEQ ID NO 3
<211> LENGTH: 20
<212> TYPE: RNA
<213> ORGANISM: Artificial Sequence
<220> FEATURE:
<223> OTHER INFORMATION: antisense_mTOR of set 2

<400> SEQUENCE: 3
gacuguggca uccaccugca                                                    20

<210> SEQ ID NO 4
<211> LENGTH: 20
<212> TYPE: RNA
<213> ORGANISM: Artificial Sequence
<220> FEATURE:
<223> OTHER INFORMATION: antisense_STAT3 of set 2

<400> SEQUENCE: 4
ugcagguagg cgccucaguc                                                    20

<210> SEQ ID NO 5
<211> LENGTH: 19
<212> TYPE: RNA

```
<213> ORGANISM: Artificial Sequence
<220> FEATURE:
<223> OTHER INFORMATION: antisense_mTOR of set 3

<400> SEQUENCE: 5
gacuguggca uccaccugc                                                19

<210> SEQ ID NO 6
<211> LENGTH: 19
<212> TYPE: RNA
<213> ORGANISM: Artificial Sequence
<220> FEATURE:
<223> OTHER INFORMATION: antisense_STAT3 of set 3

<400> SEQUENCE: 6
gcagguaggc gccucaguc                                                19

<210> SEQ ID NO 7
<211> LENGTH: 18
<212> TYPE: RNA
<213> ORGANISM: Artificial Sequence
<220> FEATURE:
<223> OTHER INFORMATION: antisense_mTOR of set 4

<400> SEQUENCE: 7
gacuguggca uccaccug                                                 18

<210> SEQ ID NO 8
<211> LENGTH: 18
<212> TYPE: RNA
<213> ORGANISM: Artificial Sequence
<220> FEATURE:
<223> OTHER INFORMATION: antisense_STAT3 of set 4

<400> SEQUENCE: 8
cagguaggcg ccucaguc                                                 18

<210> SEQ ID NO 9
<211> LENGTH: 17
<212> TYPE: RNA
<213> ORGANISM: Artificial Sequence
<220> FEATURE:
<223> OTHER INFORMATION: antisense_mTOR of set 5

<400> SEQUENCE: 9
caagcugcug uggcuga                                                  17

<210> SEQ ID NO 10
<211> LENGTH: 17
<212> TYPE: RNA
<213> ORGANISM: Artificial Sequence
<220> FEATURE:
<223> OTHER INFORMATION: antisense_STAT3 of set 5

<400> SEQUENCE: 10
ucagcuacag cagcuug                                                  17

<210> SEQ ID NO 11
<211> LENGTH: 20
<212> TYPE: RNA
<213> ORGANISM: Artificial Sequence
<220> FEATURE:
<223> OTHER INFORMATION: antisense_mTOR of set 6

<400> SEQUENCE: 11
ugcugggccg caugcgcugc                                               20
```

```
<210> SEQ ID NO 12
<211> LENGTH: 20
<212> TYPE: RNA
<213> ORGANISM: Artificial Sequence
<220> FEATURE:
<223> OTHER INFORMATION: antisense_STAT3 of set 6

<400> SEQUENCE: 12
gcagccacug cggcccagca                                              20

<210> SEQ ID NO 13
<211> LENGTH: 19
<212> TYPE: RNA
<213> ORGANISM: Artificial Sequence
<220> FEATURE:
<223> OTHER INFORMATION: antisense_mTOR of set 7

<400> SEQUENCE: 13
gcugggccgc augcgcugc                                               19

<210> SEQ ID NO 14
<211> LENGTH: 19
<212> TYPE: RNA
<213> ORGANISM: Artificial Sequence
<220> FEATURE:
<223> OTHER INFORMATION: antisense_STAT3 of set 7

<400> SEQUENCE: 14
gcagccacug cggcccagc                                               19

<210> SEQ ID NO 15
<211> LENGTH: 18
<212> TYPE: RNA
<213> ORGANISM: Artificial Sequence
<220> FEATURE:
<223> OTHER INFORMATION: antisense_mTOR of set 8

<400> SEQUENCE: 15
cugggccgca ugcgcugc                                                18

<210> SEQ ID NO 16
<211> LENGTH: 18
<212> TYPE: RNA
<213> ORGANISM: Artificial Sequence
<220> FEATURE:
<223> OTHER INFORMATION: antisense_STAT3 of set 8

<400> SEQUENCE: 16
gcagccacug cggcccag                                                18

<210> SEQ ID NO 17
<211> LENGTH: 17
<212> TYPE: RNA
<213> ORGANISM: Artificial Sequence
<220> FEATURE:
<223> OTHER INFORMATION: antisense_mTOR of set 9

<400> SEQUENCE: 17
ugggccgcau gcgcugc                                                 17

<210> SEQ ID NO 18
<211> LENGTH: 17
<212> TYPE: RNA
<213> ORGANISM: Artificial Sequence
<220> FEATURE:
```

```
<223> OTHER INFORMATION: antisense_STAT3 of set 9

<400> SEQUENCE: 18
gcagccacug cggccca                                                         17

<210> SEQ ID NO 19
<211> LENGTH: 276
<212> TYPE: DNA
<213> ORGANISM: Artificial Sequence
<220> FEATURE:
<223> OTHER INFORMATION: U7 promotor

<400> SEQUENCE: 19
cctagagtcg acactagata acaacatagg agctgtgatt ggctgttttc agccaatcag          60
cactgactca tttgcatagc ctttacaagc ggtcacaaac tcaagaaacg agcggtttta         120
atagtctttt agaatattgt ttatcgaacc gaataaggaa ctgtgctttg tgattcacat         180
atcagtggag gggtgtggaa atggcacctt gatctcaccc tcatcgaaag tggagttgat         240
gtccttccct ggctcgctac agacgcactt ccgcaa                                   276

<210> SEQ ID NO 20
<211> LENGTH: 54
<212> TYPE: DNA
<213> ORGANISM: Artificial Sequence
<220> FEATURE:
<223> OTHER INFORMATION: nucleic acid molecule encoding UUGGAUCCAA loop
      shRNA

<400> SEQUENCE: 20
gactgtggca tccacctgca tttggatcca atgcaggta ggcgcctcag tctt                54

<210> SEQ ID NO 21
<211> LENGTH: 54
<212> TYPE: DNA
<213> ORGANISM: Artificial Sequence
<220> FEATURE:
<223> OTHER INFORMATION: nucleic acid molecule encoding UUCAAGAGAG loop
      shRNA

<400> SEQUENCE: 21
gactgtggca tccacctgca tttcaagaga gatgcaggta ggcgcctcag tctt               54

<210> SEQ ID NO 22
<211> LENGTH: 19
<212> TYPE: RNA
<213> ORGANISM: Artificial Sequence
<220> FEATURE:
<223> OTHER INFORMATION: mTOR siRNA_sense strand

<400> SEQUENCE: 22
guggaaacag gacccauga                                                      19

<210> SEQ ID NO 23
<211> LENGTH: 19
<212> TYPE: RNA
<213> ORGANISM: Artificial Sequence
<220> FEATURE:
<223> OTHER INFORMATION: mTOR siRNA_antisense strand

<400> SEQUENCE: 23
ucaugggucc uguuccac                                                       19

<210> SEQ ID NO 24
<211> LENGTH: 19
```

```
<212> TYPE: RNA
<213> ORGANISM: Artificial Sequence
<220> FEATURE:
<223> OTHER INFORMATION: STAT3 siRNA_sense strand

<400> SEQUENCE: 24
uguucucuga gacccauga                                                    19

<210> SEQ ID NO 25
<211> LENGTH: 19
<212> TYPE: RNA
<213> ORGANISM: Artificial Sequence
<220> FEATURE:
<223> OTHER INFORMATION: STAT3 siRNA_antisense strand

<400> SEQUENCE: 25
ucaugggucu cagagaaca                                                    19

<210> SEQ ID NO 26
<211> LENGTH: 54
<212> TYPE: RNA
<213> ORGANISM: Artificial Sequence
<220> FEATURE:
<223> OTHER INFORMATION: UUGGAUCCAA loop shRNA

<400> SEQUENCE: 26
gacuguggca uccaccugca uuuggaucca aaugcaggua ggcgccucag ucuu             54

<210> SEQ ID NO 27
<211> LENGTH: 54
<212> TYPE: RNA
<213> ORGANISM: Artificial Sequence
<220> FEATURE:
<223> OTHER INFORMATION: UUCAAGAGAG loop shRNA

<400> SEQUENCE: 27
gacuguggca uccaccugca uuucaagaga gaugcaggua ggcgccucag ucuu             54
```